(12) United States Patent
Pilarski et al.

(10) Patent No.: US 6,956,121 B2
(45) Date of Patent: Oct. 18, 2005

(54) PREPARATION OF PAROXETINE INVOLVING NOVEL INTERMEDIATES

(75) Inventors: Gideon Pilarski, Holon (IL); Ilya Avrutov, Bat Hefer (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/137,087

(22) Filed: May 1, 2002

(65) Prior Publication Data

US 2003/0166938 A1 Sep. 4, 2003

Related U.S. Application Data

(60) Provisional application No. 60/360,760, filed on Mar. 1, 2002.

(51) Int. Cl.$^7$ .............................................. C07D 405/12
(52) U.S. Cl. ...................................... 546/197; 514/321
(58) Field of Search .......................... 546/197; 514/321

(56) References Cited

U.S. PATENT DOCUMENTS

| | | | |
|---|---|---|---|
| 4,007,196 A | | 2/1977 | Christensen et al. ......... 546/197 |
| 4,721,723 A | | 1/1988 | Barnes et al. ............... 514/321 |
| 5,874,184 A | * | 2/1999 | Takeuchi et al. ............ 429/192 |
| 6,080,759 A | | 6/2000 | Ward et al. ................. 514/321 |
| 6,228,953 B1 | * | 5/2001 | Barancyk et al. ............ 525/374 |
| 6,433,179 B1 | * | 8/2002 | Wang et al. ................ 546/197 |
| 2002/0151716 A1 | | 10/2002 | Lemmens et al. .......... 546/197 |

FOREIGN PATENT DOCUMENTS

| | | | |
|---|---|---|---|
| EP | 190496 | * | 8/1986 |
| EP | 0 810 225 A1 | | 12/1997 |
| JP | 2000-095780 | * | 4/2000 |
| WO | WO 00/78753 | | 12/2000 |

OTHER PUBLICATIONS

Greene "Protective groups in Organic Synthesis" Wiley–Intersci. p.218, 226–227, 230–231 (1982).*
Lee Tai Liu et al., "Asymmetric Syntheses of Trans–3,4–Disubstituted 2–Piperidiones and Piperidines," Tetrahedron: Asymmetry 12 (2001) 419–426.

* cited by examiner

*Primary Examiner*—Celia Chang
(74) *Attorney, Agent, or Firm*—Kenyon & Kenyon

(57) ABSTRACT

Disclosed are processes for preparing novel carbamate intermediates of paroxetine comprising dealkylating N-alkylparoxetine by reaction thereof with a haloalkyl ester of a haloformic acid, in a suitable organic solvent. Also disclosed are processes for preparing paroxetine comprising hydrolyzing the novel carbamate intermediates in a suitable solvent. Paroxetine prepared by the above processes can be neutralized with hydrogen chloride and crystallized as paroxetine hydrochloride anhydrous, hemihydrate or as a solvate of isopropanol. The invention is further directed to the novel carbamate intermediates formed by the disclosed processes.

50 Claims, No Drawings

PREPARATION OF PAROXETINE INVOLVING NOVEL INTERMEDIATES

CROSS-REFERENCE TO RELATED APPLICATIONS

This application claims the benefit of provisional application Ser. No. 60/360,760, filed Mar. 1, 2002, which is incorporated herein by reference.

FIELD OF THE INVENTION

The present invention relates to processes for the synthesis of intermediates useful in preparing paroxetine (PRX); processes for preparing paroxetine using such intermediates; and, to intermediates of the disclosed processes. More particularly, the present invention relates to a novel process for the preparation of paroxetine by dealkylation of N-alkylparoxetine, such as N-methylparoxetine (Me-PRX), and to novel intermediates of this process.

BACKGROUND OF THE INVENTION

Paroxetine (PRX), (−)-trans-3-[(1,3-benzodioxol-5-yloxy)methyl]-4-(4-fluorophenyl) piperidine; (3S, 4R)-3-[5-(1,3-dioxaindanyl)oxymethyl]-4-(p-fluorophenyl) piperidine, is a 5-hydroxytryptamine (5-HT, serotonin) re-uptake inhibitor and is useful as a therapeutic agent for various diseases, including, inter alia, depression, Parkinson's disease, anxiety disorders, obsessive-compulsive disorders, panic disorder, post-traumatic stress disorder, and pre-menstrual syndrome (PMS). Paroxetine has formula (I):

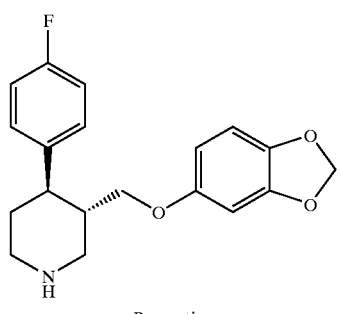

Paroxetine (I)

Example 2 of U.S. Pat. No. 4,007,196 discloses formation of paroxetine by demethylation of N-methylparoxetine (Me-PRX) having formula (II):

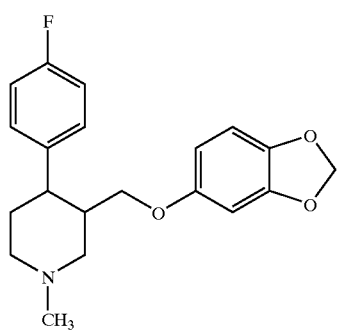

(II)

In the process disclosed in the '196 patent, Me-PRX is demethylated by reaction with phenylchloroformate in methylene chloride to form the corresponding phenyl carbamate intermediate. The phenyl carbamate intermediate is hydrolyzed to yield paroxetine by refluxing in benzene with potassium hydroxide and methyl cellosolve for four hours. Among the disadvantages of this process are the low conversion of Me-PRX to the phenyl carbamate, resulting in low yields of paroxetine. This process also results in large quantities of phenol as an undesirable by-product.

U.S. Pat. No. 4,721,723 describes a process for preparing paroxetine wherein Me-PRX is reacted with α-chloroethyl-chloroformate (1-chloroethyl-chloroformate) to form the corresponding 1-chloroethyl carbamate of paroxetine, which is then hydrolyzed under acidic conditions to yield paroxetine. A significant disadvantage of this process is the long time required for the conversion of Me-PRX to paroxetine under the conditions disclosed in, for example, Examples 6 and 7 of the '723 patent.

EP 0 810 225 A1 discloses a process for producing paroxetine by reacting Me-PRX with a lower alkyl, lower cycloalkyl, aralkyl or $C_mF_{2m+1}$ ester of haloformic acid to yield a carbamate intermediate. The corresponding carbamate intermediate is hydrolyzed in an appropriate solvent under alkaline conditions to yield paroxetine, which is extracted from the reaction mixture with an appropriate solvent such as toluene. The hydrolysis of the carbamate intermediate took from 2–3 days of reflux with alkali and produced low to moderate yields of paroxetine.

WO 00/78753 discloses forming a finely divided complex of a base (preferably potassium hydroxide), and a carbamate intermediate obtained from the demethylation of Me-PRX and refluxing in a solvent (preferably toluene) to yield paroxetine.

In view of the foregoing, a need exists in the art for a high yield and time-efficient process for the preparation of paroxetine, which does not result in harmful by-products. In particular, there exists the need for such an improved process for preparing paroxetine by demethylation of N-methylparoxetine.

SUMMARY OF THE INVENTION

In one aspect, the present invention is directed to a compound of formula (VII):

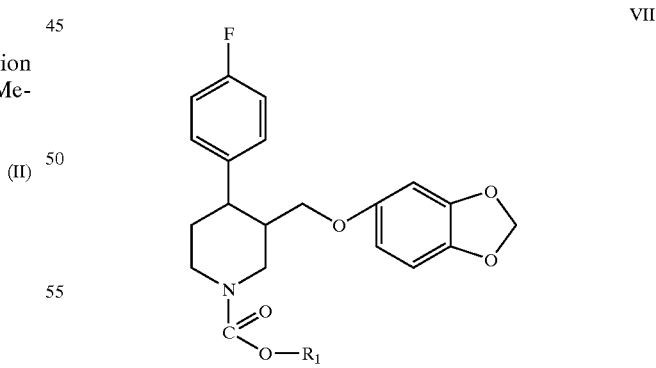

VII wherein $R_1$ is a haloalkyl other than 1-monohaloalkyl or perfluoroalkyl. In one preferred embodiment, $R_1$ is 2-chloroethyl. In another preferred embodiment, $R_1$ is 2,2,2-trichloroethyl.

In another aspect, the present invention is directed to a process for preparing a compound of formula (VII) comprising reacting a compound of formula (V) with compound of formula (VI) in a suitable organic solvent,

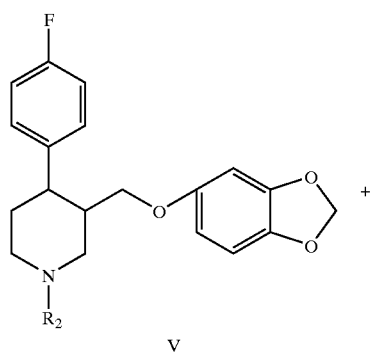

V

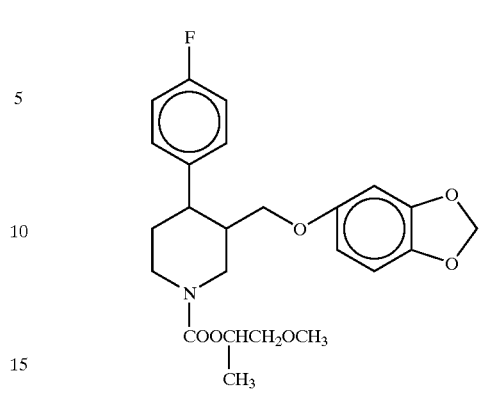

VIII

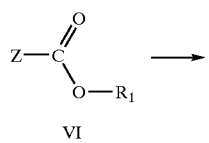

VI

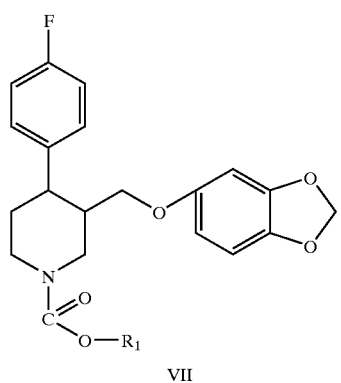

VII wherein Z is a halogen, $R_1$ is as defined above, and $R_2$ is a lower alkyl. In some preferred embodiments, Z is chlorine, $R_1$ is 2-chloroethyl or 2,2,2-trichloroethyl and $R_2$ is methyl. In another preferred embodiment, the reaction is conducted in the presence of a tertiary amine base. A particularly preferred tertiary amine base is a trialkylamine such as triethylamine or tributylamine.

In another aspect, the present invention is directed to a process for preparing paroxetine comprising hydrolyzing a compound of formula (VII), preferably under alkaline conditions. In a preferred embodiment, the hydrolysis is conducted in the presence of a glycol monoether. A particularly preferred glycol monoether is propylene glycol monomethyl ether (PGME).

In another aspect, the present invention is directed to a compound of formula (VIII):

In another aspect, the present invention is directed to a process for preparing a compound of formula (VIII) comprising hydrolyzing of a compound of formula (VII), preferably under alkaline conditions, in the presence of propylene glycol monomethyl ether (PGME).

In another aspect, the present invention is directed to a process for preparing paroxetine comprising the steps of reacting N-alkyl paroxetine with a haloformic acid ester of formula (VI) in a suitable organic solvent to form a carbamate intermediate of formula (VII), and hydrolyzing the carbamate intermediate of formula (VII), preferably under alkaline conditions, to obtain paroxetine. In a preferred embodiment, the carbamate intermediate is hydrolyzed in the presence of a glycol monoether. Paroxetine base may be recovered from the reaction mixture. An acid addition salt, preferably a pharmaceutically acceptable acid addition salt of paroxetine may then be formed from the paroxetine base. Among preferred acid addition salts of paroxetine are included, for example, paroxetine HCl in any of the various polymorphic forms of paroxetine HCl as are known in the art. Among presently preferred polymorphic forms of paroxetine HCl are included crystalline paroxetine HCl hemihydrate, anhydrous paroxetine HCl and paroxetine HCl solvates, for example the isopropanolate of paroxetine HCl.

These and other aspects of the present invention will now be described in more detail with reference to the following detailed description of the invention.

DETAILED DESCRIPTION OF THE INVENTION

In one aspect, the present invention is directed to a process for preparing a novel carbamate intermediate of paroxetine having formula (VII) wherein $R_1$ is a haloalkyl group, other than 1-monohaloalkyl or perfluoroalkyl, by the dealkylation of N-alkylparoxetine of formula (V) wherein $R_2$ is a lower alkyl.

The term "haloalkyl" refers to a $C_1$–$C_6$ alkyl group in which one or more of the carbon atoms is substituted with one or more halogen atoms. Preferred haloalkyl groups are $C_1$–$C_4$ alkyl groups in which one or more of the carbon atoms is substituted with one or more halogen atoms. The alkyl group may be a straight or branched-chain alkyl group.

The halogen atom is one or more of fluorine, chlorine, bromine and iodine. Among preferred haloalkyl groups are 2-haloalkyl groups such as 2-haloethyl and 2-halopropyl. The term "2-haloalkyl" refers to a $C_2$–$C_6$ alkyl group in which the carbon atom at the 2-position is substituted with one or more halogen atoms. Among preferred 2-haloalkyl groups are 2-chloroethyl and 2,2,2-trichloroethyl.

The term "1-monohaloalkyl" refers to a $C_2$–$C_6$ alkyl radical having only a single halogen atom, which halogen atom is at the 1-position of the alkyl radical. Thus, the term "1-monohaloalkyl," for example, does not include 1,2-dichloroethyl, 1,1-dichloroethyl or chloromethyl.

The term "perfluoroalkyl" refers to the group $C_mF_{2m+1}$, where m is an integer of from 1 to 6.

The term "lower alkyl" as used herein refers to a straight or branched chain $C_1$–$C_6$ alkyl group. Among particularly preferred lower alkyl groups, i.e., $R_2$ in the compound of formula (V), are ethyl and methyl. Where $R_2$ is methyl, the compound of formula (V) is N-methyl paroxetine (Me-PRX) having formula (II).

Compound (V) is dealkylated by reacting it with a haloformic acid ester of formula (VI), wherein Z is a halogen atom such as fluorine, chlorine, bromine or iodine, and $R_1$ is as defined above. Among preferred haloformic acid esters of formula (VI) are the 2-haloalkyl esters. A particularly preferred 2-haloalkyl ester of haloformic acid is the 2-chloroethyl ester wherein Z is chlorine, i.e., 2-chloroethyl-chloroformate ("CECF"). Another preferred haloformic acid ester is 2,2,2-trichloroethyl-chloroformate.

The dealkylation of compound (V), i.e., N-alkylparoxetine, is conducted in a suitable organic solvent. Among suitable solvents are included, for example, dichloromethane, chloroform, diethyl ether, t-butyl methyl ether, tetrahydrofuran, 1,4-dioxane, 1,2-dimethoxyethane, benzene, toluene, xylene, hexane, heptane, petroleum ether, methyl acetate, ethyl acetate, N,N-dimethylformamide and N,N-dimethylacetamide. Aromatic solvents such as toluene are among those preferred for conducting the dealkylation of compound (V). Dry toluene is a particularly preferred solvent for conducting the dealkylation reaction. For example, toluene having a water content within the range of from about 0.10% (technical grade toluene) to about 0.001% (extra dry toluene) may be used as the solvent for conducting the dealkylation.

The N-alkylparoxetine and haloformic acid ester are preferably added to toluene kept at a temperature of from about 0° C. to about 10° C., more preferably about 5° C. The reaction temperature is preferably in the range of from about 10° to about 150° C., more preferably from about 20° to about 120° C. The reaction mixture may be heated to a temperature near or, preferably, at reflux conditions and the reaction is preferably conducted for a time sufficient to effect substantially complete conversion of the N-alkylparoxetine to the corresponding carbamate. Alternatively, the haloformic acid ester may be added dropwise at the reflux temperature of the reaction mixture and continuing reflux for up to about 10 hours, or until substantially complete conversion of the N-alkylparoxetine to the corresponding carbamate has occurred. The term "substantially complete conversion" as used herein refers to conversion of about 90% or more, preferably about 95% or more and, more preferably, about 99% or more of the N-alkylparoxetine to the corresponding carbamate.

In some preferred embodiments, the dealkylation of compound (V) is conducted in the presence of a base. Examples of suitable bases include, for example, an organic amine, of which tertiary amines are preferred, an alkoxide, an alkali metal hydroxide, an alkaline earth metal hydroxide, an alkali metal hydride, an alkaline earth metal hydride or an alkali or alkaline earth metal carbonate or hydrogencarbonate salt. Specific examples of suitable bases include, for example, 1,8-bis(N,N-dimethylamino)napthalene, sodium methoxide, sodium ethoxide, sodium phenoxide, sodium hydroxide, potassium hydroxide, calcium hydroxide, magnesium hydroxide, sodium hydride, potassium hydride, calcium hydride, sodium carbonate, potassium carbonate, sodium hydrogencarbonate, potassium hydrogencarbonate, calcium carbonate and basic alumina. Preferred bases are tertiary amines such as trialkylamines of the general formula $(R)_3N$, wherein each R is the same or different $C_1$–$C_6$ straight or branched-chain alkyl. Preferred trialkylamines are tributylamine ($Bu_3N$) and triethylamine ($Et_3N$). Tributylamine is a particularly preferred trialkylamine base. As illustrated by the Examples following this description, the presence of a tertiary amine in the dealkylation reaction mixture results in an increased yield of the corresponding carbamate and decreases the time required for effecting substantially complete conversion of the N-alkylparoxetine to the corresponding carbamate.

Upon substantially complete conversion to the corresponding carbamate, the organic layer is separated, and preferably washed and dried. Water may be used to wash the separated organic layer and a suitable drying agent such as $Na_2SO_4$ may be used to dry the washed organic layer. Before separation of the organic layer, the mixture is preferably cooled, such as by adding water to cool the reaction mixture to room temperature. The preferably cooled reaction mixture is concentrated to dryness by, for example, evaporation. The resultant product is a carbamate intermediate of paroxetine having formula (VII). The compound of formula (VII) is novel compound in accordance with the present invention. A particularly preferred novel carbamate intermediate in accordance with this aspect of the present invention is a compound of formula (IV), i.e., the compound of formula (VII) wherein $R_1$ is 2-chloroethyl:

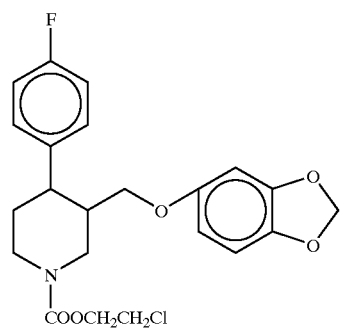

IV

This compound is referred to herein as the 2-chloroethyl carbamate of paroxetine or "CECB". Another preferred carbamate is the 2,2,2-trichloroethyl carbamate of paroxetine, which has the following structure (IX):

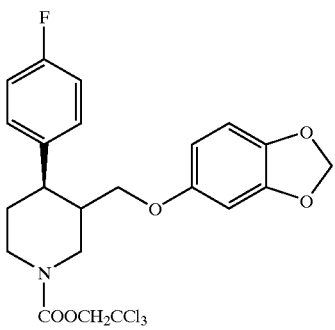

(IX)

Another aspect of the present invention is a process for preparing paroxetine by hydrolyzing a carbamate intermediate of formula (VII), preferably under alkaline conditions, to yield paroxetine.

The carbamate intermediate of formula (VII) is hydrolyzed in an appropriate solvent to yield paroxetine. The reaction temperature is preferably from 10 to 150° C., more preferably from 20 to 120° C. The reaction mixture may be heated to a temperature near or, preferably, at reflux conditions and the reaction is preferably conducted for a time sufficient to effect substantially complete conversion of the carbamate intermediate of formula (VII) to paroxetine.

The hydrolysis of the carbamate may be conducted under acidic or, preferably, under alkaline conditions. Among suitable bases for conducting the alkaline hydrolysis are included, for example, an alkoxide, an alkali metal hydroxide, an alkaline earth metal hydroxide, or an alkali or alkaline earth metal carbonate or hydrogencarbonate salt. Specific examples of suitable bases include, for example, sodium methoxide, sodium ethoxide, sodium hydroxide, potassium hydroxide, calcium hydroxide, magnesium hydroxide, sodium carbonate, potassium carbonate, sodium hydrogencarbonate, potassium hydrogencarbonate, and calcium carbonate. Preferred bases include, for example, the alkali metal hydroxides such as sodium hydroxide and potassium hydroxide and the alkaline earth metal hydroxides.

Among suitable solvents for conducting the alkaline hydrolysis of the carbamate intermediate are included, for example, diethyl ether, t-butyl methyl ether, tetrahydrofuran, 1,4-dioxane and 1,2-dimethoxyethane, benzene, toluene, xylene, hexane, heptane, petroleum ether, methanol, ethanol, isopropanol, t-butanol, glycol monoethers, water, and mixtures of any of the foregoing. Among preferred solvents for conducting the alkaline hydrolysis are included, for example, lower alkanols such as methanol, ethanol, isopropanol, t-butanol and mixtures of one or more of such lower alkanols with water; and, glycol monoethers and mixtures thereof with water and/or another solvent such as described above.

The term "glycol monoethers" refers to the mono-($C_1$–$C_6$, straight- or branched-chain)alkyl ethers of lower alkylene glycols such as, for example, ethylene glycol, propylene glycol, 1,3-butylene glycol and 2,3-butylene glycol. Among preferred glycol monoethers are, for example, ethylene glycol monomethyl ether ("methyl cellosolve", 2-methoxyethanol), ethylene glycol monoethyl ether ("ethyl cellosolve", 2-ethoxyethanol) and propylene glycol monomethyl ether ("PGME", 1-methoxy-2-propanol).

Applicants have found that conducting the hydrolysis of the carbamate intermediate of formula (VII) in the presence of a glycol monoether results in a faster and more efficient conversion of the carbamate intermediate into paroxetine as compared with, for example, the hydrolysis conducted in solvent comprising a lower alkanol or a mixture thereof with water. Moreover, these results are surprisingly achieved utilizing a lower solvent/carbamate ratio. Applicants believe, without wishing to be bound by any particular theory, that when a solvent containing ethanol or similar lower alkanol is used to conduct the alkaline hydrolysis, hydrolysis to paroxetine proceeds through a corresponding lower alkyl carbamate intermediate. It is believed that the hydrolysis of this lower alkyl carbamate intermediate is a rate-limiting step in yielding paroxetine. However, when the alkaline hydrolysis is conducted in the presence of a glycol monoether, it is believed that the hydrolysis proceeds through a different carbamate intermediate. It is believed, in accordance with HPLC-MS data, that this carbamate intermediate is formed by reesterification of the carbamate of formula (VII) with the glycol monoether. The hydrolysis of this intermediate evidently proceeds more quickly than that of the alkyl carbamate intermediate formed using a lower alkanol such as ethanol.

Accordingly, another aspect of the present invention is a process for the preparation of paroxetine comprising hydrolyzing a carbamate intermediate of formula (VII) under alkaline conditions in the presence of a glycol monoether. Applicants have found that conducting the alkaline hydrolysis of the carbamate intermediate of formula (VII) in the presence of PGME is particularly advantageous. Thus, where the glycol monoether is PGME, the present invention is directed to a novel intermediate of formula (VIII) formed during this alkaline hydrolysis:

VIII

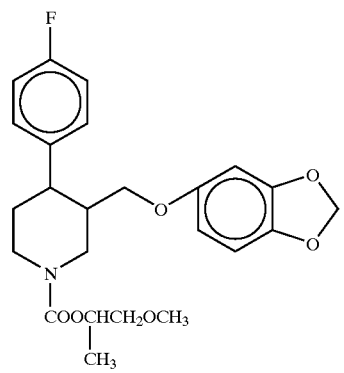

The compound of formula (VIII) is referred to herein as N-(1-methoxyprop-2-yloxycarbonyl)-paroxetine.

Table 1, below, provides comparative data obtained by conducting the hydrolysis of the carbamate intermediate of formula (IV) in (a) a solvent comprising a mixture of a lower alkanol and water and (b) a solvent comprising a mixture of a glycol monoether and water. The lower alkanols used in these examples were (i) isopropanol ("IPA"), (ii) methanol ("MeOH"), and (iii) ethanol ("EtOH"). The glycol monoethers used in these examples were (i) propylene glycol monomethyl ether ("PGME") and (ii) glycol ethyl ether ("GEE"). The base used during the alkaline hydrolysis was either sodium or potassium hydroxide.

TABLE 1

Comparative data for hydrolysis of compound (IV)

| Solvent ROH | | H₂O | Base | | Temp. | Reaction | HPLC purity profile (area %) | |
|---|---|---|---|---|---|---|---|---|
| Name | Volume | Volume | Name | eq | °C. | time, h | PRX | IV |
| IPA | 12.6 | 10 | NaOH | 7.1 | 80 | 4.5 | 72.8 | 8.3 |
| MeOH | 29 | 7 | KOH | 18.3 | 70 | 20 | 81.7 | negligible |
|  |  |  |  |  |  | 29 | 86 | negligible |
| EtOH | 12.6 | 10 | NaOH | 7.1 | 78 | 4 | 84.7 | 7.2 |
|  |  |  |  |  |  | 5.5 | 85.9 | 0.5 |
| PGME | 10 | 8 | NaOH | 7.1 | 94 | 2 | 90.3 | negligible |
|  |  |  |  |  |  | 16 | 90.4 | negligible |
| GEE | 12.6 | 10 | NaOH | 7.1 | 98 | 3 | 90.7 | 0.3 |

As evident from Table 1, when the hydrolysis of compound (IV) is conducted in a solvent comprising a mixture of a glycol monoether such as PGME or GEE and water, paroxetine yield is greater than about 90% and is achieved in a relatively short time frame of from about 2 to about 3 hours. Moreover, paroxetine formation is substantially complete in this time frame, as shown by the fact that extending the reaction time to 16 hours only resulted in a 0.1% increase (i.e., from 90.3% to 90.4%) in paroxetine yield relative to the yield obtained after reaction for 2 hours. In contrast, the paroxetine yield obtained using a solvent comprising a mixture of a lower alkanol such as IPA, MeOH or EtOH and water remains substantially lower despite a significantly longer reaction time.

In accordance with a further aspect, the present invention is directed to a process for preparing paroxetine comprising (a) dealkylating N-alkylparoxetine of formula (V) by reacting it with a haloformic acid ester of formula (VI) in a suitable solvent to form a paroxetine carbamate intermediate of formula (VII) and (b) hydrolyzing the paroxetine carbamate intermediate of formula (VII) under alkaline conditions in a suitable solvent to yield paroxetine. In a preferred embodiment, N-methylparoxetine is dealkylated by reaction with 2-chloroethylchloroformate in the presence of a trialkylamine base and the corresponding carbamate intermediate is hydrolyzed under alkaline conditions in the presence of a glycol monoether. The resultant product of the hydrolysis is paroxetine base.

Paroxetine base, in crude form, may then be recovered from the reaction mixture by, e.g., extraction into an appropriate organic solvent, such as toluene, benzene or xylene, or a mixture of any one or combination of such solvents with water. The organic phase(s) obtained from the extraction are preferably washed with, for example, water and brine. The extraction solvent may optionally be removed by, e.g., evaporation and a solution of paroxetine base in a different solvent may be formed.

Paroxetine base in solution may then be converted to a pharmaceutically acceptable acid addition salt. A preferred pharmaceutically acceptable acid addition salt is paroxetine HCl, which may be made in any of the various polymorphic forms thereof known in the art. Among the presently preferred polymorphic forms of paroxetine HCl are included crystalline paroxetine hydrochloride hemihydrate as disclosed in U.S. Pat. No. 4,721,723, which is incorporated herein in its entirety; and, any of the paroxetine hydrochloride anhydrate and solvate forms, particularly the isopropanolate, disclosed in U.S. Pat. No. 6,080,759, which is incorporated herein in its entirety.

Paroxetine base in solution may be converted into paroxetine HCl by, for example, contacting a solution of paroxetine base, such as the toluenic solution obtained from the alkaline hydrolysis and extraction steps, as described above, with aqueous or gaseous HCl followed by crystallization in an appropriate solvent to obtain the desired polymorphic form. Where the desired polymorphic form is the hemihydrate, it is preferable to contact the solution of paroxetine base with aqueous HCl followed by crystallization as generally disclosed in U.S. Pat. No. 4,721,723. Where the desired polymorphic form is anhydrous paroxetine or the ispropanolate, a solvent solution of paroxetine base is preferably contacted with dry hydrogen chloride gas or a solvent substantially free of water wherein the solvent has hydrogen chloride gas dissolved therein. U.S. Pat. No. 6,080,759 discloses methods for the preparation of anhydrous forms of paroxetine HCl. The solvents used to form the anhydrates are substantially free of water, meaning that there is insufficient water present at the time of crystallization to effect conversion to a hydrated form of paroxetine HCl such as the hemihydrate. A solvent substantially free of water may be obtained by drying the solvent with a conventional drying agent such as a molecular sieve. Anhydrous solvents may also be purchased commercially.

Thus, crude paroxetine hydrochloride hemihydrate may be formed, for example, from a toluenic solution of paroxetine base by contacting the solution of paroxetine base with aqueous HCl followed by crystallization in an appropriate solvent as generally disclosed in U.S. Pat. No. 4,721,723.

Crystalline paroxetine hydrochloride hemihydrate may then be prepared by recrystallization of the crude paroxetine hydrochloride hemihydrate in a suitable solvent. Among suitable solvents are included, for example, lower alkanols such as methanol and ethanol; ketones such as acetone; esters such as ethyl acetate; and, mixtures of any of the foregoing such as methanol/acetone.

Anhydrous forms of paroxetine hydrochloride may be formed by the methods as generally disclosed in U.S. Pat. No. 6,080,759. The anhydrous form is free of bound solvents. Anhydrous paroxetine hydrochloride may be prepared by contacting, in a dry N₂ environment, a solution of paroxetine base in an organic solvent, such as isopropanol, with dry hydrogen chloride gas. Alternatively, the solution of paroxetine base in an organic solvent may be contacted with a solvent substantially free of water wherein the solvent has dry hydrogen chloride gas dissolved therein. The reaction mixture is heated to ensure complete dissolution of the paroxetine hydrochloride. Seed crystals of anhydrous paroxetine may be added to improve the crystallization process.

As disclosed in U.S. Pat. No. 6,080,759, anhydrous forms of paroxetine free of bound solvent may also be prepared from the paroxetine hemihydrate by dissolving the hemihydrate in an appropriate solvent substantially free of water which forms an azeotrope with water. Suitably, solvent is removed by distillation and fresh solvent is added until all of the water is removed.

The anhydrous forms free of bound solvent may also be made by crystallizing paroxetine hydrochloride in an organic solvent or a mixture of solvents which form a solvate with the paroxetine hydrochloride and displacing the solvated solvent or solvents from the paroxetine hydrochloride solvate using a displacing agent. Preferably, gaseous or liquid water may be used as the displacing agent. It is important that the paroxetine hydrochloride solvate is contacted with enough water and for sufficient time to displace the solvent but insufficient to cause conversion to the hydrochloride hemihydrate.

Paroxetine HCl can also be prepared in various solvate forms as disclosed in U.S. Pat. No. 6,080,759. Among the preferred solvate forms is paroxetine hydrochloride isopropanolate as disclosed in Examples 1–3 of U.S. Pat. No. 6,080,759. Paroxetine HCl isopropanolate may be formed by displacing water from paroxetine HCl hemihydrate in, e.g., a mixture of toluene and isopropanol followed by crystallization. Paroxetine HCl isopropanolate may also be formed by contacting a solution of paroxetine base in isopropanol with dry hydrogen chloride gas followed by crystallization. The isopropanolate may also be formed by contacting a solution of paroxetine base in dry isopropanol with a solution of dry hydrogen chloride gas in dry isopropanol followed by crystallization. Solvates other than the isopropanolate can be made by similar methods as disclosed in U.S. Pat. No. 6,080,759. Among such solvates are included solvates from solvents such as alcohols other than isopropanol such as 1-propanol and ethanol; from organic acids such as acetic acid; from organic bases such as pyridine; from nitriles such as acetonitrile; from ketones such as acetone and butanone; from ethers such as tetrahydrofuran; from chlorinated hydrocarbons such as chloroform and from hydrocarbons such as toluene. These solvates may be used to form the anhydrous forms free of bound solvent by either displacing the solvent as described above or by removing the solvent by conventional techniques such as vacuum oven drying.

Recrystallization of paroxetine hydrochloride may be conducted from a solvent mixture of methanol and acetone.

The present invention is illustrated in further detail with reference to the following non-limiting Examples:

Examples 1–3 disclose the formation of the 2-chloroethyl carbamate of paroxetine ("CECB", 1-(2-chloroethoxycarbonyl)-4-(p-fluorophenyl)-3-[5-(1,3-dioxanindanyl)oxymethyl]piperidine) by reaction of N-methyl paroxetine with 2-chloroethyl-chloroformate ("CECF"). Example 4 discloses the alkaline hydrolysis of the 2-chloroethyl carbamate of paroxetine to yield paroxetine. Example 5 discloses the alkaline hydrolysis of the 2-chloroethyl carbamate of paroxetine in propylene glycol monomethyl ether ("PGME") and water. Example 6 discloses the alkaline hydrolysis of the 2-chloroethyl carbamate of paroxetine in ethanol and water. Example 7 discloses the alkaline hydrolysis of the 2-chloroethyl carbamate of paroxetine in propylene glycol monomethyl ether to form paroxetine base. Example 8 discloses the formation of 2,2,2-trichloroethyl-carbamate of paroxetine (1-(2,2,2-trichloroethoxycarbonyl)-4-(p-fluorophenyl)-3-[5-(1,3-dioxanindanyl)oxymethyl]piperidine) by reaction of N-methylparoxetine with 2,2,2-trichloroethyl-chloroformate. Example 9 discloses a multi-stage process for producing paroxetine hydrochloride hemihydrate comprising preparation of the 2-chloroethyl carbamate of paroxetine; hydrolysis thereof to yield paroxetine base; formation of crude paroxetine hydrochloride hemihydrate from the paroxetine base; and, recrystallization of the crude paroxetine hydrochloride hemihydrate to yield crystalline paroxetine hydrochloride hemihydrate. Example 10 discloses the preparation of paroxetine hydrochloride anhydrous from a solution of paroxetine base in toluene.

EXAMPLE 1

Reaction with 2-Cl-ethylchloroformate (CECF) in Dry Conditions

Me-PRX (3 g) and extra dry toluene (40 ml, less than 0.001% water) are charged into dried equipment under a dry $N_2$ stream. The reaction mixture is cooled to 4° C. with an ice bath. CECF (2.7 mL, 3 eq., purchased from SNPE) is added dropwise for several minutes. The mixture is heated to reflux for 7 hours providing the substantially complete conversion of Me-PRX (HPLC) to the carbamate. Water (50 mL) is added to cool the reaction mixture to room temperature. The organic layer is separated, washed with water, dried with $Na_2SO_4$ and evaporated to dryness to give 1-(2-chloroethoxycarbonyl)-4-fluorophenyl-3-[5-(1,3-dioxaindanyl)oxymethyl]piperidine, i.e., the 2-chloroethyl carbamate of paroxetine (CECB).

EXAMPLE 2

Reaction with CECF in the Presence of $Bu_3N$

The same procedure as described in Example 1 is repeated, except that the equipment is not previously dried, technical grade toluene (less than 0.10% water) is used instead of extra dry toluene, and the reactants are not charged under a dry $N_2$ stream. The reaction mixture, before addition of CECF, also contains 2.05 g (1.2 eq.) of $Bu_3N$. After 1.5 hours of reflux, substantially complete conversion of Me-PRX to the corresponding carbamate takes place. The carbamate, i.e., the 2-chloroethyl carbamate of paroxetine (CECB) is separated from the reaction mixture using the same procedures as described in Example 1.

EXAMPLE 3

Reaction with CECF in the Presence of $Et_3N$

The same procedure as described in Example 2 is repeated, but with 1.1 g $Et_3N$ (1.2 eq.) used in place of $Bu_3N$. After 4 hours of reflux, conversion of the Me-PRX to the corresponding carbamate is 74% (reaction stopped).

EXAMPLE 4

Reaction with CECF Without Amine

The same procedure as described in Example 1 is repeated, except that the equipment is not previously dried, technical grade toluene is used instead of extra dry toluene, and the reactants are not charged under a dry $N_2$ stream. Conversion of Me-PRX to the corresponding carbamate after 3 hours is 47% (reaction stopped).

EXAMPLE 5

Hydrolysis of CECB

A mixture of 6.13 g of the product of Example 1, 12 mL IPA, 6.5 g NaOH and 44 mL $H_2O$ are refluxed for 18 hours. At this point, the conversion of CECB to PRX is more than 95% (HPLC). The mixture is cooled and the organic phase is evaporated to give crude paroxetine with quantitative yield (95%) from Me-PRX.

EXAMPLE 6
Hydrolysis of CECB

A mixture of 4.24 g of compound (IV) (8.7 mmol), 48 ml ethanol, 2.5 g NaOH (62.5 mmol) and 38 ml water is refluxed for 4 hours. The reaction mixture contains (HPLC) 84.7% of PRX and 1.5% of (IV). After an additional 1.5 hours of reflux, the content of PRX increases only 1%.

EXAMPLE 7
Hydrolysis of CECB

A mixture of 9.8 g compound (IV) (18.3 mmol), PGME (100 mL), 5.2 g NaOH (129 mmol) and water (80 mL) is heated with stirring to 90–95° C. The stirring is continued at this temperature for 2 hours. At this point, the reaction mixture contains (HPLC) 90.3% of PRX. In the another experiment, GEE is used in place of PGME, and paroxetine is obtained in a yield of 90.7% after 3 hours.

EXAMPLE 8
Reaction with 2,2,2-trichloroethyl-chloroformate

Me-PRX (150 g) is dissolved in toluene (450 ml) at room temperature. The mixture is then heated to reflux. At reflux, 2,2,2-trichloroethyl-chloroformate (120 ml) is added dropwise for about 2.5 hours. After about 3 hours at reflux, the reaction mixture is cooled, and ammonia 20% (300 ml) and water (300 ml) is added. The organic phase is separated and washed with water (500 ml), followed by brine (500 ml). The organic phase is then separated, dried over $MgSO_4$, filtered. Toluene is then removed under reduced pressure to give 280.2 g of the 2,2,2-trichloroethyl carbamate of paroxetine. The carbamate is then hydrolyzed according to procedures set forth, for example, in Examples 5–7 to give paroxetine base. Paroxetine base may then be converted into the desired polymorphic form of, e.g., the hydrochloride acid addition salt such as the hemihydrate, anhydrate or solvate form as disclosed herein.

EXAMPLE 9
Preparation of Paroxetine Hydrochloride Hemihydrate from N-methyl Paroxetine
Preparation of CECB N-methylparoxetine (100 g) and toluene (300 ml) are charged into a one liter flask. The mixture is heated to reflux. CECF (125 g) is added dropwise during about 3 hours at reflux. Stirring at reflux of the reaction mixture is continued for about 10 hours. The mixture is cooled to room temperature. Water (75 ml) and $NH_4OH$ (75 ml) are added to the reaction mixture. The mixture is heated to 40° C. and stirred for 30 minutes. The organic phase is separated, washed twice with water (2×100 ml) and with brine (100 ml). Toluene is replaced with isopropyl alcohol during distillation and the carbamate (CECB) is filtered and dried to give 117 g CECB.
Preparation of PRX Base CECB (100 g), PGME (500 ml) and KOH (180 g) are charged into a one liter flask. The mixture is heated to 60° C. and stirred at this temperature for about 10 hours. PGME is removed by distillation at a temperature of 70° C. under vacuum. Water (470 ml) and toluene (470 ml) are added to the remaining mixture. The organic phase is separated and the aqueous phase is washed with toluene (290 ml). The combined toluene phases are washed with water (2×290 ml) and with brine (290 ml). The toluene solution of PRX base (761 g, assay by titration 9.89%) is obtained, which is used in the next step without evaporation.
Preparation of Paroxetine Hydrochloride Hemihydrate Crude The toluenic solution of PRX base (500 g), PGME (81 ml), water (81 ml), ammonium chloride (21.9 g) and hydrochloric acid 32% (14.94 g) are charged into a one liter flask. The mixture is cooled to 2–4° C. and stirred at this temperature for about 3 hours (precipitation starts after about 1 hour). The precipitate is filtered, washed consecutively with 50 ml water, 50 ml toluene and 50 ml acetone, and dried to give 49.5 g of crude PRX HCl hemihydrate.
Preparation of Crystalline Paroxetine Hydrochloride Hemihydrate Crude paroxetine hydrochloride hemihydrate (40 g), acetone (400 ml) and methanol (20 ml) are charged into a one liter flask. The mixture is heated to reflux to dissolve the crude PRX HCl hemihydrate. Stirring is continued for 15 minutes. The hot solution is filtered through a charcoal bed. The filter cake is washed with 5 ml of a mixture of acetone and methanol (20:1). The combined filtrates are cooled to 2–3° C. and stirred for 1.5 hours. The precipitate is filtered, washed with 40 ml acetone and dried to give 35 g of crystalline PRX HCl hemihydrate.

EXAMPLE 10
Preparation of Paroxetine Hydrochloride Anhydrous

A solution of paroxetine base in toluene (355 g, 9.9% w/w) is charged into a batch stirred reactor. The solvent is distilled under reduced pressure at a temperature not higher than 90° C. The distillation is continued until distillate is no longer observed. Nitrogen gas is purged into the reactor to obtain ambient pressure. A nitrogen environment is maintained throughout the conversion to paroxetine hydrochloride anhydrous.

Isopropanol extra dry (80 mL, water content less than 0.01%) is charged into the reactor. Isopropanol is then distilled under reduced pressure until distillate is no longer observed. Nitrogen gas is then purged into the reactor to obtain ambient pressure. The process of feeding isopropanol extra dry and distilling under reduced pressure is repeated two additional times. After the end of the third distillation, isopropanol extra dry (598.4 grams) and isopropanol solution (91.94 grams) containing 3.31 grams of hydrogen chloride gas are charged into the reactor under an inert nitrogen environment. The reaction mixture is heated to 70° C. to obtain complete dissolution of the paroxetine hydrochloride. After achieving fall dissolution at 70° C., the solution is cooled to 51° C. At 51° C., the solution is seeded with crystals of paroxetine hydrochloride anhydrous to facilitate the crystallization process. After the seeding, the solution is stirred at 51° C. and subsequently cooled to 25° C. over 12 hours. After the temperature of the reaction mixture reaches 25° C., the mixture is stirred for an additional hour. The resultant slurry is filtered under nitrogen and dried to give 25.4 g paroxetine hydrochloride anhydrous. Even though this Example crystallizes out of isopropanol, the product is paroxetine hydrochloride anhydrous rather than the isopropanolate. The main reason for obtaining anhydrous form rather than the isopropanolate is the use of extra dry isopropanol along with a dry atmosphere throughout the process.

Relative to Example 1 wherein $Bu_3N$ is not present, Example 2 shows that the presence of $Bu_3N$ reduces the reaction time necessary to obtain substantially complete conversion of Me-PRX to the corresponding carbamate. The same procedure with $Et_3N$ (Example 3) also reduces the reaction time relative to that required for substantially complete conversion of Me-PRX to the carbamate in Example 1. In Example 3, reflux for four hours in the presence of $Et_3N$ produces a 74% conversion to the carbamate while in the Comparative Example, conducted in the absence of $Et_3N$, only a 47% conversion is achieved. These results demonstrate a significant advantage in conducting the dealkylation of paroxetine, e.g., the demethylation of paroxetine, to achieve a compound (VII) in accordance with the present invention, when the dealkylation is conducted in the presence of a tertiary amine such as $Bu_3N$ or $Et_3N$.

Having thus described the invention with reference to particular preferred embodiments and illustrated it with examples, those in the art may appreciate modifications to the invention as described and illustrated that do not depart from the spirit and scope of the invention as disclosed in the specification.

What is claimed is:

1. A compound of formula (VII):

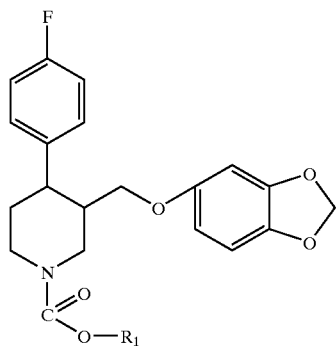

wherein $R_1$ is 2-chloroethyl or 2,2,2-trichloroethyl.

2. The compound of claim 1, wherein $R_1$ is 2-chloroethyl.

3. The compound of claim 1, wherein $R_1$ is 2,2,2-trichloroethyl.

4. A process for preparing a compound of formula (VII) comprising reacting a compound of formula (V) with a compound of formula (VI) in a suitable organic solvent,

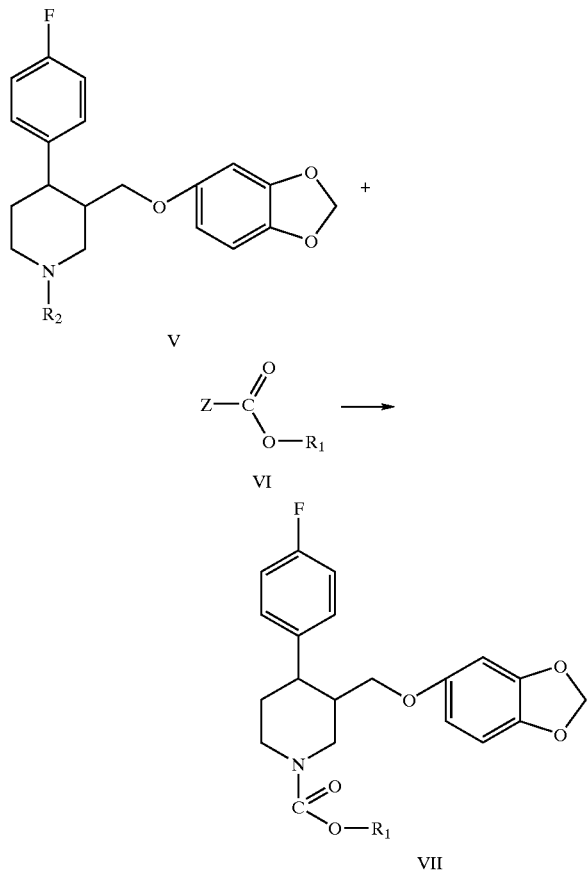

wherein Z is a halogen;

wherein $R_1$ is 2-chloroethyl or 2,2,2-trichloroethyl, and $R_2$ is a lower alkyl.

5. The process of claim 4, wherein $R_1$ is 2-chloroethyl.

6. The process of claim 4, wherein $R_1$ is 2,2,2-trichloroethyl.

7. The process of claim 4, wherein Z is chlorine.

8. The process of claim 4, wherein $R_2$ is methyl.

9. The process of claim 4, wherein the reaction is carried out in the presence of a base.

10. The process of claim 9, wherein the base is a trialkylamine.

11. The process of claim 10, wherein the trialkylamine is selected from the group consisting of tributylamine and triethylamine.

12. The process of claim 11, wherein the trialkylamine is tributylamine.

13. A compound of formula (VIII):

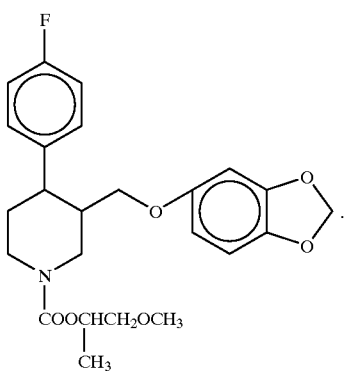

14. The compound of claim 13, wherein the compound is isolated.

15. A process for preparing a compound of formula (VIII):

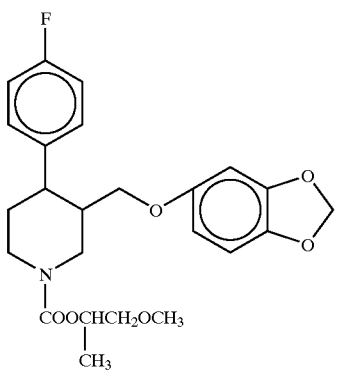

comprising hydrolyzing a compound of formula (VII) of claim 1 in the presence of propylene glycol monomethyl ether.

16. The process of claim 15, wherein $R_1$ is 2-chloroethyl.

17. The process of claim 15, wherein $R_1$ is 2,2,2-trichloroethyl.

18. A process for preparing paroxetine comprising the steps of:

(a) reacting a compound of formula (V) with a compound of formula (VI) in a suitable organic solvent, to form a compound of formula (VII), wherein Z is a halogen;

wherein $R_1$ is 2-chloroethyl or 2,2,2-trichloroethyl; and $R_2$ is a lower alkyl; and (b) hydrolyzing the compound of formula (VII) to obtain paroxetine.

19. The process of claim 18, wherein $R_2$ is methyl, $R_1$ is 2-chloroethyl and Z is chlorine.

20. The process of claim 18, wherein $R_2$ is methyl, $R_1$ is 2,2,2,-trichloroethyl and Z is chlorine.

21. The process of claim 18, wherein step (a) is carried out in the presence of a trialkylamine selected from the group consisting of tributylamine and triethylamine.

22. The process of claim 18, wherein the trialkylamine is tributylamine.

23. The process of claim 18, wherein step (b) is carried out in the presence of a glycol monoether selected from the group consisting of ethylene glycol monomethyl ether and propylene glycol monomethyl ether.

24. The process of claim 23, wherein the glycol monoether is propylene glycol monomethyl ether.

25. The process of claim 18, further comprising recovering paroxetine base from step (b).

26. The process of claim 25, further comprising preparing an acid addition salt of paroxetine from the recovered paroxetine base.

27. The process of claim 26, wherein the acid addition salt of paroxetine is paroxetine HCl hemihydrate.

28. The process of claim 27, wherein the paroxetine HCl hemihydrate is formed by contacting a solution of paroxetine base in a solvent with aqueous hydrochloric acid followed by crystallization of the hemihydrate.

29. The process of claim 28, wherein the solvent is toluene.

30. The process of claim 28, further comprising recrystallizing the hemihydrate.

31. The process of claim 30, wherein the recrystallization is conducted in a solvent mixture of methanol and acetone.

32. The process of claim 26, wherein the acid addition salt is paroxetine HCl isopropanolate.

33. The process of claim 32, wherein the paroxetine HCl isopropanolate is formed by contacting paroxetine base in solution in isopropanol with gaseous hydrochloric acid and crystallizing paroxetine HCl isopropanolate from the solvent.

34. The process of claim 32, wherein the paroxetine HCl isopropanolate is formed by contacting a solution of paroxetine base in a isopropanol with a solution of hydrogen chloride gas in isopropanol.

35. A process for preparing paroxetine comprising hydrolyzing a compound of formula (VII):

wherein $R_1$ is 2-chloroethyl or 2,2,2-trichloroethyl.

36. The process of claim 35, wherein $R_1$ is 2-chloroethyl.

37. The process of claim 35, wherein $R_1$ is 2,2,2-trichloroethyl.

38. The process of claim 35, wherein the hydrolysis is conducted in the presence of a glycol monoether.

39. The process of claim 38, wherein the glycol monoether is selected from the group consisting of ethylene glycol monomethyl ether and propylene glycol monomethyl ether.

40. The process of claim 39, wherein the glycol monoether is propylene glycol monomethyl ether.

41. The process of claim 35, further comprising recovering paroxetine base.

42. The process of claim 41, further comprising preparing an acid addition salt of paroxetine from the recovered paroxetine base.

43. The process of claim 42, wherein the acid addition salt of paroxetine is paroxetine HCl hemihydrate.

44. The process of claim 43, wherein the paroxetine HCl hemihydrate is formed by contacting a solution of paroxetine base in a solvent with aqueous hydrochloric acid followed by crystallization of the hemihydrate.

45. The process of claim 44, wherein the solvent is toluene.

46. The process of claim 44, further comprising recrystallizing the hemihydrate.

47. The process of claim 46, wherein the recrystallization is conducted in a solvent mixture of methanol and acetone.

48. The process of claim 42, wherein the acid addition salt is paroxetine HCl isopropanolate.

49. The process of claim 48, wherein the paroxetine HCl isopropanolate is formed by contacting a solution of paroxetine base in isopropanol with gaseous hydrochloric acid and crystallizing paroxetine isopropanolate from the solvent.

50. The process of claim 48, wherein the paroxetine HCl isopropanolate is formed by contacting a solution of paroxetine base in isopropanol with a solution of hydrogen chloride gas in isopropanol.

* * * * *